United States Patent [19]
Fountain

[11] Patent Number: 5,879,703
[45] Date of Patent: *Mar. 9, 1999

[54] ENCAPSULATION OF ACTIVE INGREDIENTS INTO LIPID VESICLES

[75] Inventor: Michael W. Fountain, Tampa, Fla.

[73] Assignee: Fountain Pharmaceuticals, Inc., Largo, Fla.

[*] Notice: The term of this patent shall not extend beyond the expiration date of Pat. No. 5,269,979.

[21] Appl. No.: 507,401

[22] PCT Filed: Feb. 25, 1994

[86] PCT No.: PCT/US94/02053

§ 371 Date: Jan. 2, 1996

§ 102(e) Date: Jan. 2, 1996

[87] PCT Pub. No.: WO94/18950

PCT Pub. Date: Sep. 1, 1994

[51] Int. Cl.[6] ............................. A61K 9/127; A61K 9/107
[52] U.S. Cl. ............................. 424/450; 514/937; 264/4.1
[58] Field of Search ................................... 424/450, 451; 264/4.1; 514/937

[56] References Cited

U.S. PATENT DOCUMENTS

| | | |
|---|---|---|
| 1,695,599 | 12/1928 | Merzoian . |
| 2,261,877 | 11/1941 | Erickson et al. . |
| 2,712,400 | 7/1955 | Stauffer . |
| 3,780,911 | 12/1973 | Paige . |
| 4,588,578 | 5/1986 | Fountain et al. . |
| 4,610,868 | 9/1986 | Fountain et al. . |
| 4,755,375 | 7/1988 | Kozam . |
| 4,900,549 | 2/1990 | De Vries et al. . |
| 5,049,388 | 9/1991 | Knight et al. . |
| 5,100,662 | 3/1992 | Bolcsak . |
| 5,133,965 | 7/1992 | Fountain . |
| 5,269,979 | 12/1993 | Fountain . |

FOREIGN PATENT DOCUMENTS

| | | |
|---|---|---|
| B-91166/82 | 4/1982 | Australia . |
| 0356340 | 2/1990 | European Pat. Off. . |
| 8911850 | 12/1989 | WIPO . |
| 9308834 | 5/1993 | WIPO . |

OTHER PUBLICATIONS

Guzman, et al., "Antibody responses in the serum and respiratory tract of mice following oral vaccination with liposomes coated with filamentous hemagglutinin and pertussis toxoid," *Infect Immun* 61:573–579 (1993).

Sato, et al., "Separation and purification of the hemagglutinins from *Bordetella Pertussis,*" *Infect Immun* 41:313–320 (1983).

Schuster, et al., "Production of antibodies against phosphocholine, phosphatidylcholine, sphingomyelin, and lipid A by injection of liposomes containing lipid A," *J Immunology* 122:900–905 (1979).

*Primary Examiner*—Raj Bawa
*Attorney, Agent, or Firm*—Sidley & Austin

[57] ABSTRACT

A method for preparation of a shelf-stable precursor solution used to prepare a vaccine delivery system and useful for remote encapsulation of active ingredients is described. The vaccine delivery system utilizes solvent dilution microcarriers into which pathogen subunits are incorporated for delivering antigens to mucosal sites for stimulating imunoglobulin production.

5 Claims, 1 Drawing Sheet

ENCAPSULATION OF ACTIVE INGREDIENTS INTO LIPID VESICLES

TECHNICAL FIELD OF THE INVENTION

This invention relates to a system for delivering vaccines to mucosal sites for the stimulation of immunoglobulin production and to the production of vaccines and lipid-encapsulated active ingredients.

BACKGROUND OF THE INVENTION

The route of administration of a particular vaccine is dependent upon several factors. Factors to be considered include locus of initiation of infection, locus of disease progression, systemic or nonsystemic involvement, pathogenicity of the particular vaccine used, and type of immunity desired to be induced. Vaccines have been given orally, parenterally, and through inhalation. Oral and inhalation administration of vaccines is preferable when it is desirous to stimulate production of secretory immunoglobulin as a first line of defense against infection. Oral administration of vaccines may also be preferable in the instance of a particularly pathogenic organism, even though the organism has been attenuated prior to administration.

As the pathogenicity of the particular organism administered as a vaccine increases, so do concerns regarding incomplete attenuation. Alternatives have been developed which utilize protein subunits of antigenic molecules expressed on the surface of the organisms instead of the complete organism. However, although such materials are generally antigenic, they are not always immunogenic. Immunogenicity depends upon, among other factors, size. Several attempts have been made to address the antigen immunogen dichotomy in particularly pathogenic organisms. In that regard, various adjuvants were developed to augment the immunogenicity of a particular antigen and include such materials as keyhole limpet hemocyanin, aluminum hydroxide gels, sodium alginate, synthetic polynucleotides, muramyl dipeptide, Bordetella pertussis, Freund's Complete Adjuvant (emulsion of mineral oil, water, and mycobacterial extracts, and Freund's Incomplete Adjuvant (emulsion of water and oil only). Liposomes have also been used as adjuvants.

A liposome is a lipid-containing vesicle capable of entrapping various molecules of interest. Previously, most liposome vesicles functioned as adjuvants on the principle of entrapment of the antigen within a central core. However, liposomes have been developed which attempt to integrate the antigen within the lipid bi-layer.

U.S. Pat. No. 5,100,662 issued to Bolcsak et al. on Mar. 31, 1992 describes liposomes or liposome-like structures comprising sterols either alone or in combination with additional liposome-forming lipids. Liposome structures such as micelles, reverse micelles, hexagonal phases, multilamellar vesicles, or unilamellar vesicles are described. The liposomes may be prepared with or without the use of an organic solvent and may function as vaccines after entrapment or association of an immunogen.

While not specifically addressed to vaccine preparations, U.S. Pat. No. 5,049,388 issued to Gilbert et al. on Sep. 17, 1991 describes small particle aerosol liposomes and liposome-drug combinations for medical use and discloses that the drug or medication is interactive with the liposome membrane so that, on its rupture, the drug or medication is not lost from the liposome. Before aerosolization, the liposomes are heterogenous in size.

U.S. Pat. No. 4,900,549 issued to de Vries on Feb. 13, 1990, relates to a process for preparing immunogenic complexes. The patent describes an amphipathic antigenic protein or peptide contacted with a solution containing a detergent, a sterol, and a glycoside comprising hydrophobic and hydrophilic regions. Subsequently, the detergent is removed and the immunogenic complex is purified. Optionally, the solution further comprises a phospholipid, preferably phosphatidylethanolamine. The structure is described as consisting of cage-like or two-dimensional aggregates, depending upon whether phospholipid is or is not present, respectively.

The incorporation of pathogen subunits into liposome preparations for stimulation of immune response has been described previously. More specifically, the incorporation of a soluble antigen extract of Brucella abortus and the lipopolysaccharide (LPS) of Salmonella abortus equi, Escherichia coli, and Serratia marcescens. Fountain, et al., "Effect of Phosphatidylcholine Liposomes Containing Brucella abortus Soluble Antigen on the Response of Bovine Lymphocytes to Phytohemagglutinin," *Current Microbiology*, Vol. 6, pp. 61–64, 1981. These preparations involved incorporation of the antigens into a phosphatidylcholine liposome preparation described in Schuster et al., "Production of Antibodies Against Phosphocholine, phosphatidylcholine, Sphingomyelin and Lipid A by Injection of Liposomes Containing Lipid A," *American Journal of Immunity*, Vol. 122, pp. 4003–4009, 1979, and involved the entrapment of the subunit within the liposome.

Conventional liposome preparations, i.e., those entrapping the molecule of interest, are not satisfactory for vaccine formation for several reasons. They are generally heterogeneous in size and difficult to sterilize for in vivo applications. Their stability or shelf life is often very limited. Further, the selection of passenger molecules for entrapment may be limited.

A new liposome was developed consisting of an amphipathic vehicle called a solvent dilution microcarrier (SDMC) which enables the integration of the particular molecule into the bi-layer of the lipid vesicle itself, or in association with the component of the bi-layer, rather than inside the space created by the spherical bi-layer upon formation of the vesicle. The preparation of SDMCs is described in U.S. Pat. No. 5,133,965 issued to Michael W. Fountain on Jul. 28, 1992.

Specifically, U.S. Pat. No. 5,133,965 describes a method for preparing SDMCs exhibiting substantial size homogeneity and capable of being sterilized by a variety of methods, including heating or UV radiation.

It has been found that, through a modification of the method described in U.S. Pat. No. 5,133,965, the preparation of immunogenic complexes between SDMCs and normally non-immunogenic or weakly immunogenic antigens can be effected. Additionally, it has been found that immunogenic complexes between SDMCs and the subunits of pathogens can be formed. Further, the use of SDMCs facilitates the administration of the immunogens so prepared by a variety of means, including oral ingestion and nasal inhalation.

It has further been found that a shelf-stable SDMC precursor solution can be prepared and stored at room temperature until it is desired to add the antigenic material to be utilized in the vaccine. The SDMC precursor solution can be used in a method for remote encapsulation of other active ingredients as well, which active ingredients are inherently heat-labile, solvent intolerant or unstable over time. Thus, the SDMC precursor can be kept as a stock item and used to freshly prepare encapsulated actives of interest.

SUMMARY OF THE INVENTION

In one aspect, the invention relates to a method for delivering antigens to mucosal tissue sites to stimulate the production of both secretory immunoglobulin and systemic immunoglobulin production. The method involves the integration of antigens into the lipid bi-layer of SDMCs. The SDMC-integrated antigens can then be administered in a manner effective for contacting the SDMC-integrated antigens with mucosal tissue sites.

In another aspect, the invention relates to a method for preparing immunogens from subunits of pathogens. The method involves the integration of the pathogen subunits into the lipid bi-layer of an SDMC utilizing a step-wise addition of pathogen subunits and SDMC precursor solution.

In a further aspect, the invention relates to a vaccine delivery system for delivering antigens to specific mucosal locations thereby initiating a secretory and systemic immunoglobulin response. The vaccine delivery system is an SDMC having an antigen integrated within its lipid bi-layer.

In another embodiment, a shelf-stable SDMC precursor solution is provided which may be used in a method for encapsulating active ingredients at a location or time remote from the preparation of the shelf-stable precursor solution.

DETAILED DESCRIPTION

Figure 1:
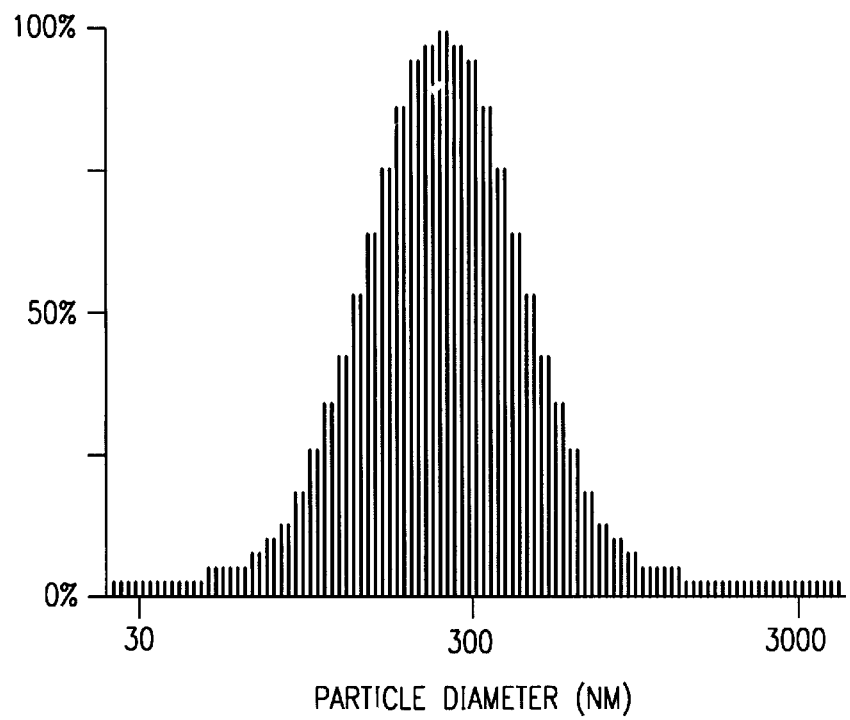
FIG. 1 depicts the size distribution of SDMC/FHA particles prepared according to the invention.
Figure 2:
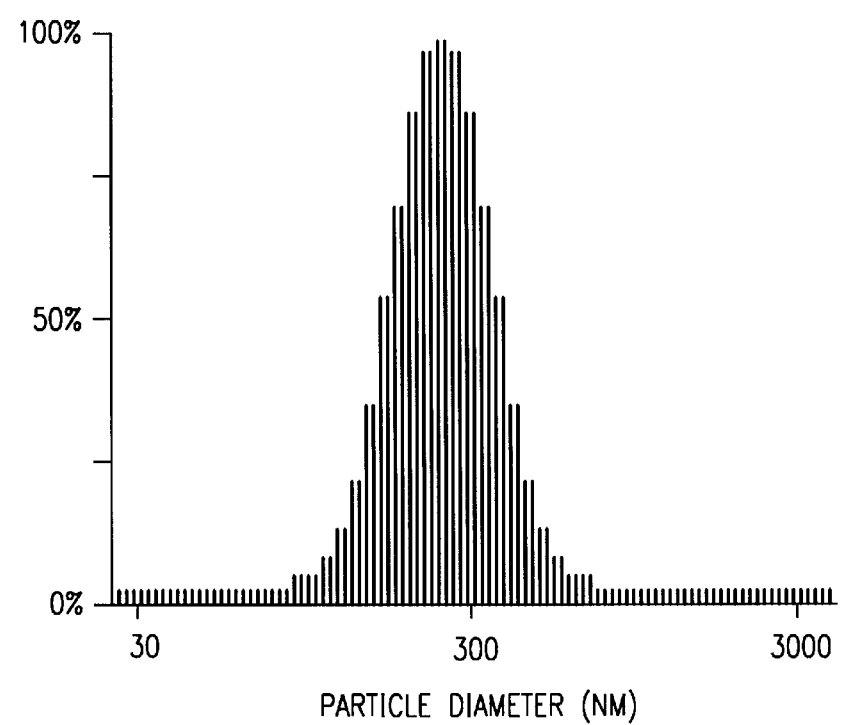
FIG. 2 depicts the size distribution of SDMC/PT particles prepared according to the invention.

This invention pertains to the use of SDMCs in vaccines. SDMCs, SDMC precursor solutions, and their preparation, are described in U.S. Pat. No. 5,133,865 issued to Fountain on Jul. 28, 1992, incorporated herein by reference. A modification of this technique accommodates the integration of antigens, specifically protein subunits of bacteria, into SDMCs for the preparation of vaccines. The subunits of other pathogens can also be incorporated. For example, lipopolysaccharides (LPS) from bacteria such as *Bordetella pertussis, Escherichia coli, Salmonella abortus equi,* and *Serratia marcescens,* soluble antigen extract of *Brucella abortus,* outer membrane proteins, capsular antigens, viral coat proteins, surface coat proteins from gram positive bacteria such as streptococcus and staphyloccus, pneumococcal antigens, and pili and/or fembri proteins, can all be incorporated into SDMCs. This list is meant to be illustrative, not exhaustive.

Specifically, an SDMC precursor solution is first prepared. The precursor solution is prepared by solubilizing a phospholipid material containing the following phosphatides: phosphatidylcholine, phosphatidylethanolamine, phosphatidic acid and phosphatidylinositol at an approximate ratio of 6.5:2.5:0.7:0.3 in ethanol, one gram of the phospholipid material to between about 5.0–7.5 mls of the ethanol solvent. The phosphatides, preferably, can consist of purified soybean phosphatides and were supplied by American Lecithin Company of New York, N.Y. Water is then added to the phospholipid/solvent mixture to form a turbid suspension. A second quantity of solvent, in this instance ethanol, is added to the turbid suspension until the suspension turns clear. An SDMC precursor solution result which is characterized by having optical clarity at room temperature and being monophasic at room temperature.

The combination of SDMC precursor solution with the antigen is then performed in a step-wise fashion. It was found that a combination in this manner obviated the organization step required in U.S. Pat. No. 5,133,865, and assured proper integration of the antigen for immunogenic presentation. Specifically, the antigens were thus incorporated either into the lipid bi-layer itself, or associated with the surface, for effective immune presentation.

The antigens can be soluble, insoluble, or polydispersable. Solubility is defined as solubility in water. It was found that the step-wise addition enables the incorporation of all three types of antigens into the SDMCs. In the particular case of insoluble and polydispersable antigens, the step-wise addition forces an interaction between the antigen and the lipid bi-layer. With polydispersable antigens, the interaction is primarily physical. With insoluble antigens, the interaction is primarily chemical, but does not involve bonding. With soluble antigens, a chemical bonding takes place.

The volume of precursor solution to be added depends upon the solubility of the antigen. The volume of precursor solution required increases with decreasing solubility of the antigen, and can be readily determined.

In a preferred embodiment, five hundred micrograms of soluble antigen is processed at a given time with the precursor solution. The antigen is mixed with a volume of precursor solution in a ratio of one volume of antigen to five volumes of precursor solution. The material is vortexed after each addition of precursor and antigen solution. The antigen and precursor solution are combined in this fashion until the desired amount of antigen has been processed. In this manner, the antigens are integrated into the lipid bi-layer. Vesicles of substantial size homogeneity, which are ready for administration, are prepared. Vesicle sizes range from about 200–400 nm were obtained.

After combination of the antigen and precursor solution, unincorporated antigen is removed by size exclusion chromatography. The final vaccine preparation is passed over a sephadex G-25 column. The SDMC-integrated antigens (vesicles) are excluded from the gel bed and are recovered in the void volume. The unintegrated antigens are retained in the vacuum. Size determinations of the SDMC-integrated antigens are performed using a Coulter submicron particle analyzer N4MD (Coulter Electronics Inc., Hialeah, Fla.).

When the antigens to be incorporated are weakly immunogenic, or tolerogenic, adjuvants can also be incorporated into the vesicles. For example, antigens consisting of LPS associated with 2% outer membrane protein from *Shigella boydii, Shigella dysenteriae* type 1, *Shigella flexneri,* and *Shigella sonnei,* give weak immune responses. In such an instance, muramyl di- or tri-peptide, lipid A, or lipid A derivatives can be incorporated into the lipid bi-layer during preparation, i.e., through incorporation into the precursor solution. Alternatively, non-specific immunostimulants, such as mitogens, can be incorporated.

The vesicles can be administered nasally by aerosolization such as by pumping from a sprayer or trigger pump. Alternatively, the vesicles can be administered orally.

The SDMC precursor solution described above can also be used as a stock solution for end or middle users such as hospitals, physicians, pharmaceutical manufacturers, agricultural users and others. These end or middle users can employ the stock SDMC precursor to encapsulate various active agents such as the vaccine agents, medicinal agents, herbicidal agents and the like. The method of encapsulating active agents using the stock SDMC precursor is especially suitable for unstable, heat-labile, or solvent-intolerant active ingredients. U.S. Pat. No. 5,133,965 discloses a method for making a stable SDMC precursor solution containing actives or passenger molecules as they are termed therein. The '965 method would not be suitable, however, to prepare a shelf-stable precursor if the active is not shelf-stable as well.

In the present method, lipid is dissolved in an organic solvent appropriate to effect the complete dissolution thereof and which is compatible with the desired application. Water is added to form a turbid suspension. Additional organic solvent is added of either the same or different type to form an optically clear, shelf-stable (at room temperature) SDMC precursor solution. The precursor is preferably packaged such as, for example, in quart plastic bottles or inert 55-gallon storage drums, and can be transported to the site of end use or middle use. It may be appropriate for a mid-user to encapsulate an active in a manufacturing facility, which active has enough stability that when encapsulated, the capsulated active can be sold as a consumer product to be used in a matter of months or weeks. Alternatively, the active of interest may have such a limited stability so that it must be encapsulated at or near the site of end use, and used immediately. The SDMC precursor solution of this invention provides for that versatility. In addition, it may be easily shipped in commerce since it does not contain actives, the shipping thereof which may be difficult due to regulations pertaining to interstate commerce and exporting.

The invention may be better understood by the following examples which are intended to be illustrative thereof.

EXAMPLE 1

Preparation of filamentous hemagglutinin (FRA) vaccine

FHA was purified from *Bordetella pertussis* as described by Sato et al., "Separation and Purification of the Hemagglutinins from *Bordetella pertussis,*" *Infection and Immunity*, Vol. 41, pp. 313–320, 1983. FHA was supplied by Gesellschaft Fur Biotechnologiesche Forshung, Germany. The initial concentration of FHA was 0.5 mg/ml in 20 mM sodium chloride, pH 7.6. A total volume of 3.2 mls of the antigen were utilized. FHA was mixed in 1 ml aliquots and added to 200 microliters of SDMC precursor solution. The mixture was vortexed after each addition of antigen/precursor solution. The final material consisted of 4 ml–3.2 ml FHA and 800 microliters of precursor solution. The final concentration of FHA was 400 $\mu$g/ml. The SDMC-integrated FHA (SDMC/FHA) vesicle size was measured in the Coulter counter as discussed above. The size distribution for the FHA/SDMC is depicted in FIG. 1. The mean size was 236 nanometers. The 95% confidence limits were 219–253 nanometers.

EXAMPLE 2

Preparation of the pertussis toxin vaccine (PT)

Pertussis toxin was supplied by S. Cryz of the Swiss Serum and Vaccine Institute, Bern, Switzerland. The concentration of pertussis toxin was 100 micrograms/ml. The toxin was supplied in 20 mM sodium chloride, pH 7.6. The original volume was 28.8 mls. Five milliliter aliquots of the toxin were added to one milliliter of precursor solution and vortexed. The final product consisted of 28.8 ml PT with 5.7 ml of precursor. Final concentration of the PT was 83.5 micrograms/ml. The size distribution of the particles prepared is depicted in FIG. 2. The SDMC-integrated PT (SDMC/PT) vesicle size was measured in the Coulter counter as discussed previously. The mean diameter of the SDMC/PT vesicles was 244 nanometers. The 95% confidence limits were 226–262 nanometers.

EXAMPLE 3

Immunization

Five-six week old female BALB/c mice (Charles Rivers) were orally immunized with FHA, SDMC/FHA, PT, and SDMC/PT. One dose of 4 micrograms of protein was given on day 0 and day 4, followed by a booster of an identical dose on day 30. Prior to administration, the mice were deprived of water for 6–8 hours and then orally given 50 microliters of the vaccine diluted in phosphate buffered saline and an equal volume of 3% sodium bicarbonate in phosphate buffered saline, pH 8.0, to achieve the desired dose. Animals were anesthetized with ether and sacrificed by cervical dislocation ten days after the booster. Blood samples were collected, the serum was separated and stored at −20° C. until testing. Lung wash samples were collected by pertrachael cannulation and gentle washing with 0.7 ml of ice-cold PBS containing 2 mM phenyl-methyl-sulfonyl fluoride as a methyl protease inhibitor. About 0.5 ml of lung wash was recovered from each mouse. Lung washes were centrifuged at 4° C. at 10,000×g for five minutes to remove debris and then stored at −20° C.

EXAMPLE 4

Antibody determinations

Enzyme linked immunosorbent assays were performed to determine the presence of FHA and PT specific antibodies. Nunc Maxisorp Immunomodule 96-well plates were coated with FHA or PT diluted in 0.1M $NaHCO_3$ (pH 9.6) at 60 mg in 50 microliters per well and incubated at 4° C. overnight. The plates were blocked with 100 microliters of 10% fetal calf serum (ICN-Flow Biomedicals) in PBS for two hours at 37° C. After washing three times with PBS, 100 microliters of the serum diluted 1:50 or lung wash diluted 1:10, in 10% fetal calf serum in PBS was added to the wells. The plates were incubated for 60 minutes at 37° C. and then washed with PBS. One hundred microliters of alkaline phosphatase-conjugated goat anti-mouse antibodies for IgG, IgM, or IgA (Southern Biotechnology Associates, Inc.) diluted 1:500 in 10% fetal calf serum in PBS was added to each well. The wells were incubated for two hours at 37° C., the plates were washed, and 100 microliters of substrate solution was added. The substrate solution consisted of 10 mgs of p-nitrophenylphosphate per ml having disodium salt in diethanolamine buffer, pH 9.8. Incubations were performed for 30 minutes at room temperature 22°–27° C. The reaction was stopped by the addition of 50 microliters of 3.0M sodium hydroxide. Absorbance at 405 nanometers was measured.

The results obtained indicated that both serum and mucosal antibody responses were elicited. Mucosal responses were determined by lung washes. IgG, IgM, and IgA antibodies were detected. Antibody responses were compared with responses obtained by immunizations with FHA and PT alone as controls. The antibody responses with SDMC/FHA were approximately three times higher than the FHA protein alone for all three antibody classes in serum, and for IgG and IgA in the lung washes. Similar results were obtained with SDMC/PT.

Immunizations were also performed intranasally using SDMCs having the lipopolysaccharide (SDMC/LPS) or outer membrane protein (SDMC/OMP) of *Bordetella pertussis* incorporated therein. These intranasal immunizations were compared with oral immunizations of the same materials. For intranasal immunization, mice were anesthetized by ether and 50 microliters of vaccine (vesicle preparation) diluted in phosphate-buffered saline was then deposited on the external nares and allowed to be inhaled. Dilutions resulting in does of 4 μg protein for SDMC/OMP and 15 μg dry weight for SDMC/LPS were performed. The dilution will be determined by the dose desired and can be from about 1:2 to about 1:1000.

Antibody titers in lung washer from nasal and oral immunizations were similar. Secretory antibody was detected 75 days after immunization. A booster was given at day 30. It was also found that the immune response could be primed a second time with the booster.

The above results indicate that 1) pathogen subunits integrated into SDMCs are immunogenic, 2) pathogen subunits integrated into SDMCs are effective at targeting mucosal tissue for eliciting secretory response, 3) SDMCs serve as effective vaccine delivery systems for stimulating both secretory and systemic immune response even when administered non-parenterally and 4) the immune response thus stimulated has longevity and can be boosted.

EXAMPLE 5

Preparation of Shelf-Stable Precursor Solution and Demonstration of Stability Over Time An SDMC precursor solution was prepared by the following method. It was determined that vesicles could be prepared at different time intervals following precursor preparation, and that these vesicles would have similar characteristics.

To examine the stability of SDMC forming precursor solution six replicate lots of precursor solution were prepared by adding 30.6 kg of soy lecithin into 96 kg of ethanol. This mixture was accomplished in a stainless steel mixing vessel with a slow rotation propeller. Mixing was conducted at room temperature. To the mixture of soy lecithin in ethanol was added 9 kg of water to form a turbid suspension. 37.7 kg of ethanol was then added to form the final SDMC precursor solution. The SDMC precursor solution was removed from the mixing vessel and stored in storage drums and sealed. Aliquots of each of the lots of precursor solution were removed prior to sealing of the storage drums and resampled twenty-four months later. SDMC forming precursor solutions were converted into SDMCs by dilution of 1 ml of each precursor solution into 10 mls of water. A Coulter N-4 submicron particle analyzer was used to determine the mean size of SDMCs from each of the samples. Results show that SDMC forming precursor solutions are stable for at least twenty-four months, exhibiting only a slight increase in the mean diameter of SDMCs over time.

TABLE 1

| SDMC Precursor Forming Solutions | Size (Mean Diameter nm) | |
| --- | --- | --- |
| | Time: 0 | Time: 24 months |
| 1 | 329 | 408 |
| 2 | 229 | 325 |
| 3 | 281 | 382 |
| 4 | 379 | 389 |
| 5 | 311 | 403 |
| 6 | 358 | 412 |
| mean | 315 | 386 |

EXAMPLE 6

Use of Shelf-Stable SDMC Precursor Solution for Remote Encapsulation of Vaccines A shelf-stable SDMC precursor solution, such as the one exemplified in Example 5 or another prepared according to the method of the invention given herein can be used as a base ingredient to which a vaccine of interest can be added at a remote location and/or a remote time.

The SDMC precursor can be prepared and held at room temperature. It can be shipped to another locale and a protein subunit component of an antigen added to the precursor solution at least up to two years, and perhaps longer after the precursor solution was prepared. The precursor solution is suitable as long as it does not separate over time out of a monophase. The precursor solution can be mixed with the antigen in a ratio of about one volume dissolved antigen to five volumes of precursor solution in a step-wise fashion until the quantity of antigen desired is fully integrated into vesicles. Unincorporated antigen can be removed by size-exclusion chromatography.

EXAMPLE 7

Use of Shelf-Stable SDMC Precursor Solution for Remote Encapsulation of Epidermal Growth Factor or Other Small Peptides or Proteins The method described in Example 6 can also be used to prepare encapsulated peptides or proteins which are desirable for topical application to the skin or mucosa.

If desired, other agents may be added such as moisturizers or other accepted pharmaceutical carriers.

EXAMPLE 8

Use of Shelf-Stable SDMC Precursor Solution for Remote Encapsulation of Heat Labile, Unstable, or Solvent Intolerant Active Ingredients The method of the present invention can be used for preparing SDMCs which can be quickly prepared to deliver active ingredients which are unstable, heat labile or solvent intolerant. The shelf-stable SDMC precursor serves as a stock solution or base, and the active ingredient can be added thereto just weeks, days or moments prior to use. This preparation method provides the advantage of a prepared precursor to which a laboratory, pharmacy, agricultural station or manufacturer can add the active ingredient so that the finished SDMCs have a shelf-stable time frame appropriate for the shelf stability of the active ingredient. The finished product may be sold for the purpose the active ingredient is appropriate for and applied accordingly. For example, an agricultural preparation of herbicidal actives in SDMCs may be sprayed onto leaves of undesired plants. An SDMC preparation containing vitamin C active ingredients may be prepared and administered to a patient immediately by injection or topically. A sunscreen agent or sun-filtering agent could be added to the precursor solution to provide a SDMC useful for skin protection from ultraviolet exposure.

The previous examples are meant to be illustrative of the invention and are not meant to limit the invention in any manner. It will be apparent to those skilled in the art that various modifications are available and it is intended to cover such modifications as fall within the scope of the appended claims.

I claim:

1. A method for encapsulating active ingredients into a lipid vesicle, comprising the steps of:

mixing an active ingredient with a precursor solution to form a loaded precursor mixture, said precursor solution having been made according to the steps of:

(i) solubilizing an amphipathic material in a first quantity of a non-aqueous solvent appropriate to solubilize the amphipathic material to form a firs t mixture;

(ii) adding a quantity of water to said first mixture in an amount sufficient to form a turbid suspension; and (iii) adding a second quantity of an appropriate non-aqueous solvent to said turbid suspension in a sufficient amount to cause a second mixture comprising said precursor solution to form, said precursor solution characterized by having optical clarity at room temperature and being monophasic at room temperature.

2. The method of claim 1, further comprising the step of diluting said loaded precursor mixture in an excess of water to form solvent dilution microcarrier vehicles loaded with said active ingredient.

3. The method of claim 1, further comprising the step of mixing said loaded precursor mixture with air to form solvent dilution microcarrier vehicles loaded with said active ingredient.

4. A precursor solution made according to the steps of:
   (a) solubilizing an amphipathic material in a first quantity of a non-aqueous solvent appropriate to solubilize the amphipathic material to form a first mixture;
   (b) adding a quantity of water to said first mixture in an amount sufficient to form a turbid suspension; and
   (c) adding a second quantity of an appropriate non-aqueous solvent to said turbid suspension in a sufficient amount to cause a second mixture comprising said precursor solution to form, said precursor solution characterized by having optical clarity at room temperature and being monophasic at room temperature.

5. The precursor solution of claim 4, further comprising a container holding said precursor solution, said container affixed to or accompanying by a label which provides directions for mixing said precursor solution with an active ingredient to form solvent dilution microcarrier vehicles.

\* \* \* \* \*

UNITED STATES PATENT AND TRADEMARK OFFICE
CERTIFICATE OF CORRECTION

PATENT NO. : 5,879,703
DATED : Mar. 9, 1999
INVENTOR(S) : Michael W. Fountain.

It is certified that error appears in the above-identified patent and that said Letters Patent is hereby corrected as shown below:

Col. 2, line 16, after "*marcescens*", insert --have been reported--.

Col. 3, line 28, change "SDMC/FHA" to "SDMC/filamentous hemagglutinin (FHA)".

Col. 3, line 30, change "SDMC/PT" to "SDMC/pertussis toxin vaccine(PT)".

Col. 3, line 65, change "result" to "results".

Col. 4, line 33, change "range" to "ranging".

Col. 4, line 64, after "such as", delete "the".

Col. 5, line 24, after "actives", delete "the shipping thereof which".

Col. 5, line 24, after "actives" insert --whereas the shipment of SDMCs containing actives--.

Col. 5, line 32, after "hemagglutinin", change "(FRA)" to "(FHA)".

Col. 5, line 50, change "FHA/SDMC" to "SDMC/FHA".

Col. 5, line 61, after "volume", insert --of toxin--.

Col. 6, line 49, change "mgs" to "mg".

Col. 7, line 8, change "does" to "doses".

Col. 7, line 12, change "washer" to "washes".

Col. 7, line 47, after "Results", insert --exemplified in Table 1--.

UNITED STATES PATENT AND TRADEMARK OFFICE
CERTIFICATE OF CORRECTION

PATENT NO. : 5,879,703
DATED : Mar. 9, 1999
INVENTOR(S) : Michael W. Fountain.

It is certified that error appears in the above-identified patent and that said Letters Patent is hereby corrected as shown below:

Col. 8, line 55, after "available", insert --,--.

Col. 8, line 67, Claim 1, change "firs t" to "first".

Col. 10, line 15, Claim 4, after "accompanying", delete "by".

Signed and Sealed this

Tenth Day of April, 2001

Attest:

NICHOLAS P. GODICI

Attesting Officer

Acting Director of the United States Patent and Trademark Office